(12) United States Patent
Boudries et al.

(10) Patent No.: US 8,161,830 B2
(45) Date of Patent: Apr. 24, 2012

(54) METHOD, APPARATUS, AND SYSTEM FOR INTEGRATED VAPOR AND PARTICULATE SAMPLING

(75) Inventors: Hacene Boudries, Wilmington, MA (US); Ralph Reda, Concord, MA (US); Natalya O. Hall, Allston, MA (US); Joseph Chiffy, Nashua, NH (US); Marcel Benz, Cambridge, MA (US); Karl Goedecke, Everett, MA (US)

(73) Assignee: Morpho Detection, Inc., Newark, CA (US)

( * ) Notice: Subject to any disclaimer, the term of this patent is extended or adjusted under 35 U.S.C. 154(b) by 401 days.

(21) Appl. No.: 12/276,118

(22) Filed: Nov. 21, 2008

(65) Prior Publication Data

US 2010/0126284 A1 May 27, 2010

(51) Int. Cl.
*G01N 1/22* (2006.01)
(52) U.S. Cl. .................................................. 73/863.12
(58) Field of Classification Search ............... 73/863.12, 73/863.13, 863.11
See application file for complete search history.

(56) References Cited

U.S. PATENT DOCUMENTS

| | | | |
|---|---|---|---|
| 5,092,219 A | 3/1992 | Rounbehler et al. ........... 86/50 |
| 6,345,545 B1 | 2/2002 | Linker et al. | |
| 6,523,393 B1 | 2/2003 | Linker et al. | |
| 6,619,143 B2 | 9/2003 | Danylewych-May et al. | |
| 6,708,572 B2 | 3/2004 | Jenkins et al. | |
| 6,884,997 B2 | 4/2005 | Kashima et al. | |
| 7,244,288 B2 | 7/2007 | Belyakov et al. | |
| 7,299,710 B2 * | 11/2007 | Syage ........................ 73/863.12 |
| 7,338,638 B2 | 3/2008 | McGann et al. | |
| 7,401,498 B2 * | 7/2008 | Syage et al. ................. 73/28.01 |
| 2004/0094707 A1 | 5/2004 | Jenkins et al. ................ 250/288 |
| 2005/0120776 A1 | 6/2005 | Jenkins et al. | |
| 2006/0196249 A1 | 9/2006 | Syage et al. | |
| 2007/0034024 A1 | 2/2007 | Syage | |
| 2008/0073503 A1 | 3/2008 | Wu | |
| 2008/0250877 A1 | 10/2008 | Wu | |

FOREIGN PATENT DOCUMENTS

WO 2007113486 A1 10/2007
WO 2008060666 A2 5/2008

OTHER PUBLICATIONS

International Searching Authority, Patent Cooperation Treaty, Notification of Transmittal of the International Search Report and the Written Opinion of the International Searching Authority, or the Declaration; The International Search Report and the Written Opinion for Application No. PCT/US2009/065075, Aug. 18, 2010, 13 pages.

(Continued)

*Primary Examiner* — Hezron E Williams
*Assistant Examiner* — Tamiko D Bellamy
(74) *Attorney, Agent, or Firm* — Armstrong Teasdale LLP

(57) ABSTRACT

A detection system for identifying an unknown substance includes a detector assembly configured to receive a particulate or vapor and determine a substance contained within the collected vapor or particulate sample, and at least one heater element operatively coupled in flow communication with the detector assembly. The heater element is configured to attract an airborne vapor when the detection system is in a vapor mode, and desorb at least a portion of the attracted particulate when the detection system is in a particulate mode.

17 Claims, 7 Drawing Sheets

OTHER PUBLICATIONS

Voiculescu, et al., Micropreconcentrator for Enhanced Trace Detection of Explosives and Chemical Agents, Oct. 1, 2006, pp. 1094-1104, IEEE Sensors Journal, IEEE Service Center, New York, NY, DOI:10.1109/JSEN.2006.881431, vol. 6, No. 5., ISSN: 1530-437X, XP002493890.

Hannum, et al., Miniaturized Explosives Preconcentrators for use in Man-Portable Explosives Detection Systems, Oct. 23, 2000, pp. 222, 224, 226, IEEE 34th Annual 2000 International Carnahan Conference on Oct. 23-25, 2000, Piscataway, NJ, Security Technology, 2000, ISBN: 978-0-7803-5965-9, XP010527867.

\* cited by examiner

METHOD, APPARATUS, AND SYSTEM FOR INTEGRATED VAPOR AND PARTICULATE SAMPLING

STATEMENT REGARDING FEDERALLY SPONSORED RESEARCH & DEVELOPMENT

The U.S. Government may have certain rights in this invention as provided for by the terms of Contract No. W91CRB-6-C-0001.

BACKGROUND OF THE INVENTION

The field of the invention relates generally to methods and systems for trace detection, and more particularly, to integrated vapor and particulate sampling.

Some known trace detection apparatus use two distinct sampling systems, one optimized for vapor sampling and another separate system used for particulate sampling. Such trace detection apparatus either collect samples of analyte by physically removing microscopic particles from surfaces or by collecting and concentrating vapors from the air.

Within such trace detection apparatus, microscopic particles of explosives, drugs or other compounds of interest are removed or harvested by using a sampling device, such as for example a cloth, paper strip, swab or other particle-trapping device. The sampling device is wiped over a surface of interest, then placed into a desorption device which is in communication to a trace chemical detector, such as an ion mobility spectrometer. The sampling device and trapped particles are heated in the desorption device (desorber) to the point where such particles are vaporized. The vapor generated in the desorber is channel to the chemical detection system for analysis.

Explosive vapors, chemicals weapon agents, toxic industrial compounds, illicit drugs and other targeted compounds such as hydrocarbons can also be detected by sensing vapors emitted from the substance. In some known vapor sampling systems, a volume of air is typically collected onto a pre-concentrator. A pre-concentrator adsorbs target molecules from air flowing at a high rate and relatively large volume, allowing molecules from substances not of interest to pass through to an exhaust line. The adsorbing medium is flash heated to vaporize the analyte into a low volume and channeled continuously via a desorbtion airflow, which is directed into a detector such as an ion mobility spectrometer. This process allows the target molecules present in the large air volume initially sampled into the preconcentrator to be concentrated into a much smaller air volume greatly increasing the concentration.

However, analyzing particulate or vapor presents requires a user to physically remove one sampling system, connect the other and recalibrate the apparatus. Moreover, many such systems require different operating temperatures for vapor and particle analysis. Changing temperatures from particle to vapor detection mode requires time to allow the detector temperature to stabilize and may require a system recalibration. Furthermore, after vapor collection, pre-concentrators may be heated quickly to a single, high-temperature set point to volatilize the collected compounds. This may result in the thermal decomposition of some targeted substances.

BRIEF SUMMARY OF THE INVENTION

In one aspect, a detection system for identifying an unknown substance is provided. The detection system includes a detector assembly configured to receive a sample vapor and determine a substance contained within the vapor, and at least one heater element operatively coupled in flow communication with the detector assembly. The heater element is configured to attract an airborne sample when the detection system is in a vapor mode, and desorb by flash heating the element at least a portion of the attracted sample to allow its detection.

In another aspect, an apparatus for integrated particle and vapor sampling is provided. The apparatus includes a plurality of heater elements positioned in a desorption chamber, wherein the apparatus is configured to attract a quantity of an airborne sample, and desorb a quantity of the collected airborne sample to form a concentrated vapor as well as having the capability of heating an external particulate sampling device and thus desorbing at least some of the sampled particulates as a vapor.

In yet another aspect, a method for identifying an unknown substance using an integrated particle and vapor sampling device is provided. The method includes collecting a sample on a surface of at least one of a heater element or a sampling trap, heating either to a first temperature such that the portion of the sample with the lowest vaporization temperature is desorbed from the surface, and channeling that first portion via a carrier gas to a detection device to facilitate determining a substance contained within the desorbed first portion.

BRIEF DESCRIPTION OF THE DRAWINGS

Non-limiting and non-exhaustive embodiments are described with reference to the following figures, wherein like reference numerals refer to like parts throughout the various views unless otherwise specified.

DETAILED DESCRIPTION OF THE INVENTION

Figure 1:
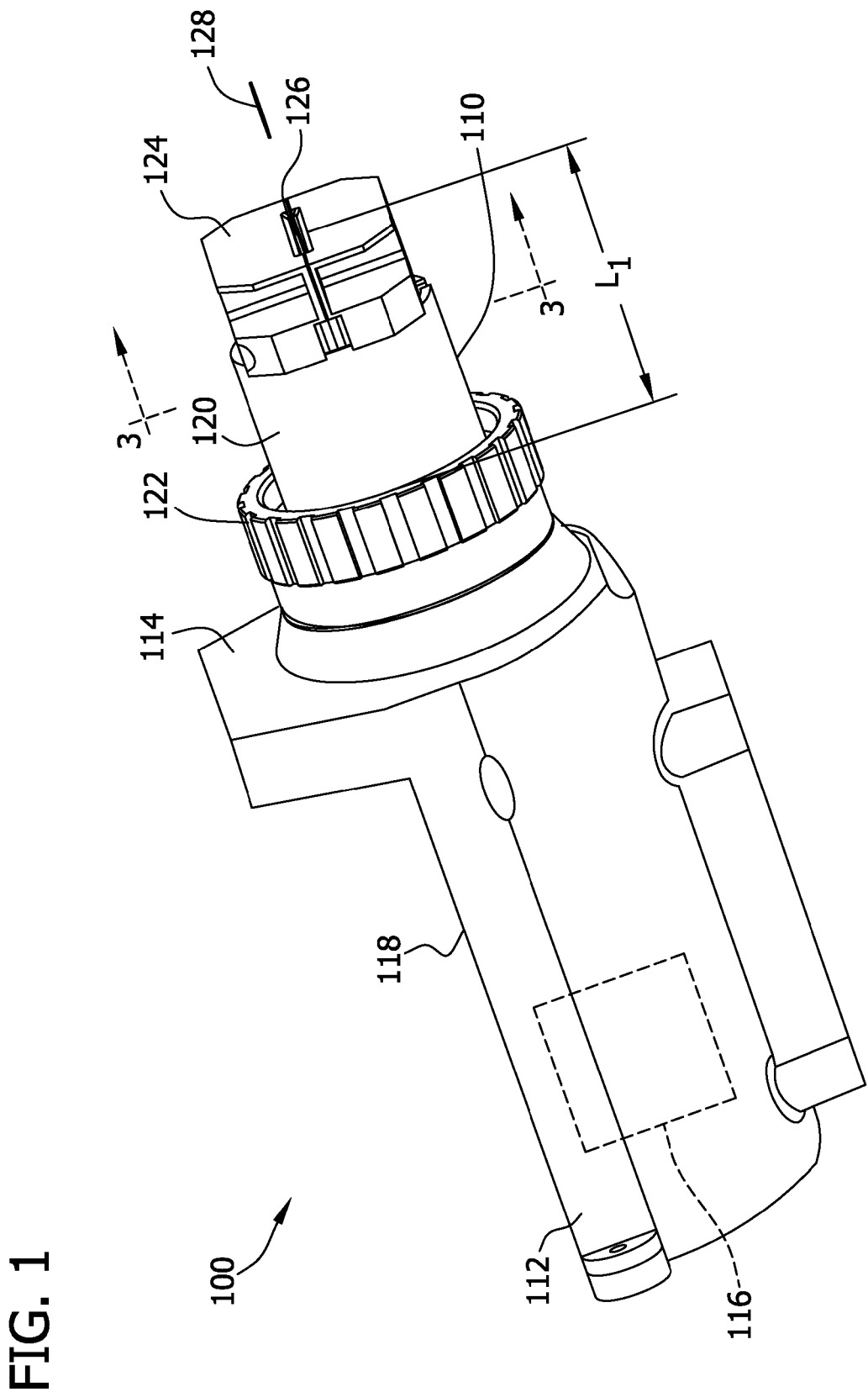
FIG. 1 is a perspective view of an exemplary detection system.

FIG. 1 is a perspective view of an exemplary detection system 100 configured to assess the chemical composition and/or biological nature or identity of an unknown substance or material to facilitate identifying potential chemical threats and/or potential biological threats. In the exemplary embodiment, detection system 100 is a desktop-type device that incorporates vapor sampling and particle sampling into an integrated device, such as an ion mobility spectrometer. Alternatively, detection system 100 may be used with any type of trace detector. In an alternative embodiment, detection system 100 may be a handheld device.

In the exemplary embodiment, detection system 100 includes a desorption chamber 110 operatively coupled to a detector assembly 112. More specifically, and in the exemplary embodiment, detector assembly 112 includes side panel 114 having a channel (not shown in FIG. 1) positioned thereon to enable a quantity of air to be channeled into detector assembly 112 using a sampling pump 116 for identifying an unknown substance or material. Desorption chamber 110 is coupled to and extends outward from side panel 114, and more specifically is substantially centered about and extends outward from the channel. Alternatively, the channel may be positioned on any surface that enables detection system 100 to function as described herein, such as for example a top surface 118 of detector assembly 112.

Desorption chamber 110 includes an outer shell 120 that extends axially a distance $L_1$ from a mounting element 122 that is used to couple desorption chamber 110 to detector assembly 112. In the exemplary embodiment, outer shell 120 is substantially cylindrical in shape and includes a distal end 124 having a slot 126 therein. Slot 126 is sized and oriented to receive a sampling trap 128 therein for use in sampling particles collected thereon, as described in more detail herein. Additionally, and in the exemplary embodiment, slot 126 is sized and oriented to allow a quantity of air to be channeled into desorption chamber 110, and into detector assembly 112 for vapor and/or particulate sampling. In an alternative embodiment, outer shell may include a plurality of slots 126 that are used to separately sample particulate and vapor, respectively, as described in more detail herein.

Figure 2:
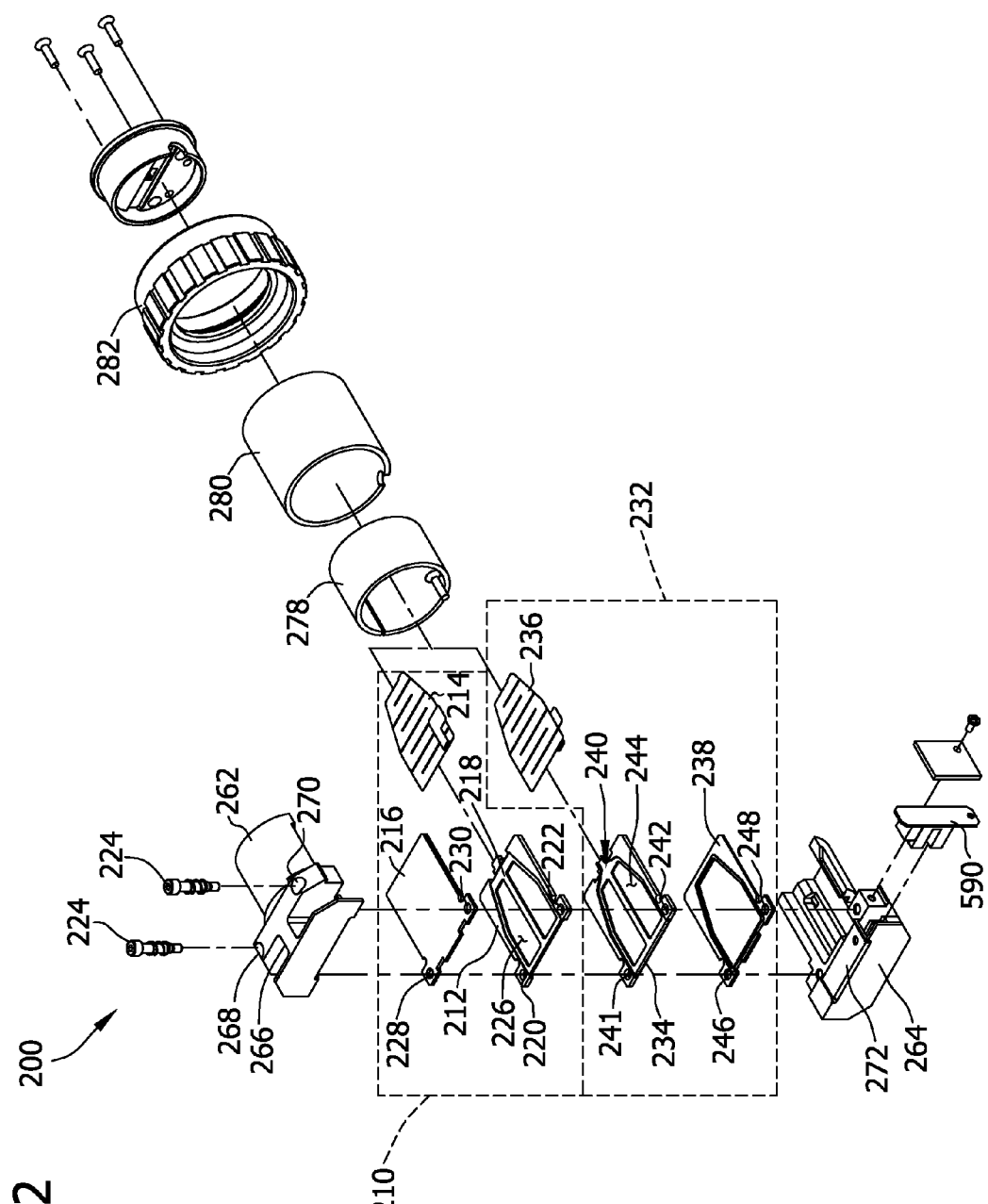
FIG. 2 is an exploded isometric view of an exemplary desorption chamber used with the exemplary detection system shown in FIG. 1.
Figure 3:
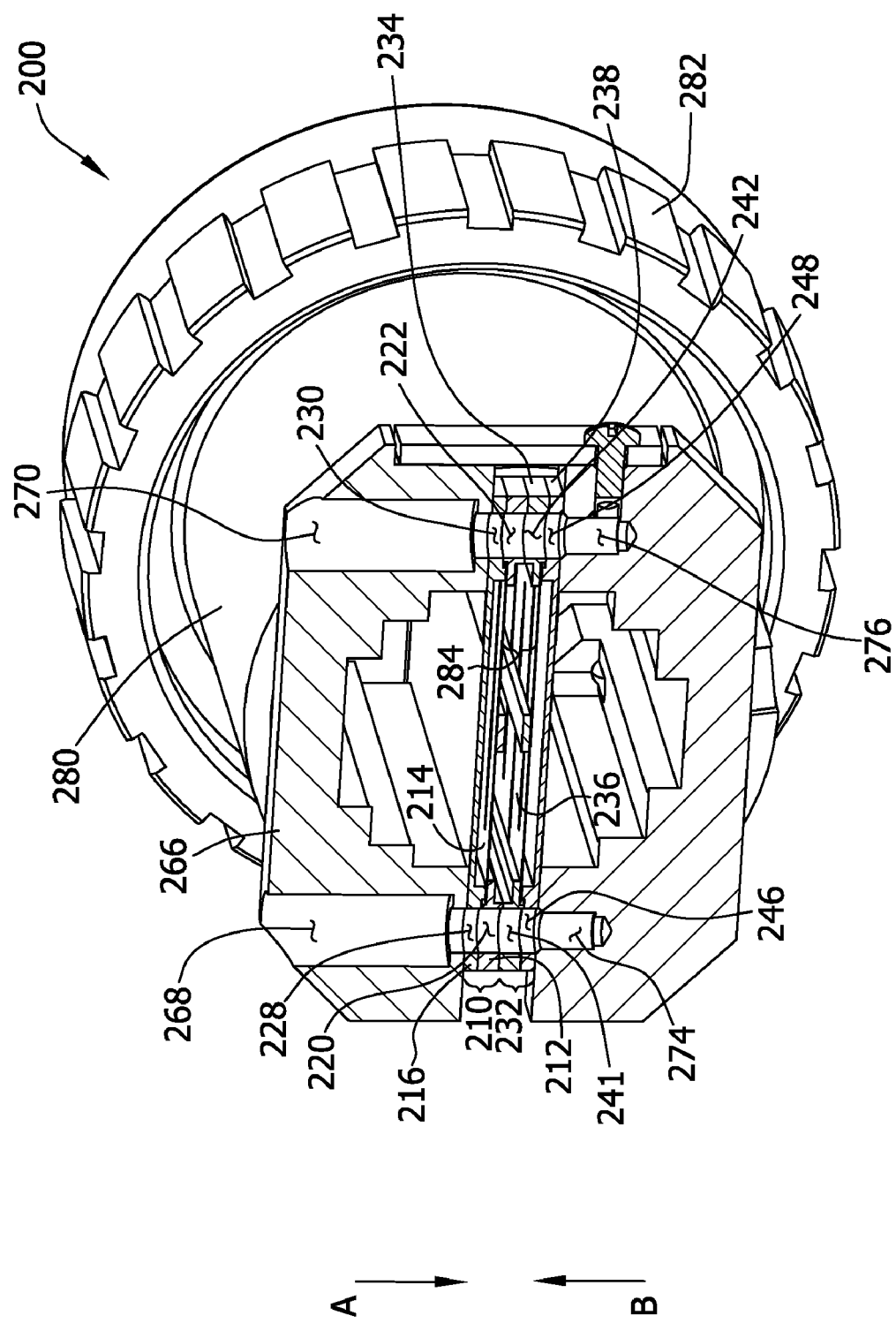
FIG. 3 is a sectional view along line 3-3 shown in FIG. 1 of an exemplary desorption chamber used with the exemplary detection system shown in FIG. 1.

FIG. 2 is an exploded view of an exemplary desorption chamber 200 used with exemplary detection system 100 shown in FIG. 1. FIG. 3 is a sectional view along line 3-3 shown in FIG. 1 of exemplary desorption chamber 200 used with exemplary detection system 100 shown in FIG. 1. Referring now to FIGS. 2 and 3, in the exemplary embodiment, desorption chamber 200 includes a first heating assembly 210 that includes a first frame element 212 that is sized to receive a first heater element 214 thereon, and a first retention plate 216. More specifically, and in the exemplary embodiment, first frame element 212 includes a recess 218 that is sized to receive first heater element 214 therein and maintain first heater element 214 in a substantially fixed position. First frame element 212 includes a first coupling aperture 220 and a second coupling aperture 222 that are each sized and oriented to receive a fastener 224 therethrough, as described herein. First frame element 212 includes a substantially hollow center 226 that allows first heater element 214 to emit heat in a first direction A during operation, as described in more detail herein. First retention plate 216 is positioned adjacent to first heater element 214 when inserted within recess 218, and is sized and oriented to maintain first heater element 214 within recess 218. In the exemplary embodiment, first retention plate 216 includes a first coupling aperture 228 and a second coupling aperture 230 that are each sized and oriented to receive fastener 224 therethrough, as described herein.

In the exemplary embodiment, desorption chamber 200 includes a second heating assembly 232 that includes a second frame element 234 that is sized to receive a second heater element 236 thereon, and a second retention plate 238. More specifically, and in the exemplary embodiment, second frame element 234 includes a recess 240 that is sized to receive second heater element 236 therein and maintain second heater element 236 in a substantially fixed position. Second frame element 234 includes a first coupling aperture 241 and a second coupling aperture 242 that are each sized and oriented to receive fastener 224 therethrough, as described herein. Second frame element 234 includes a substantially hollow center 244 that allows second heater element 236 to emit heat in a second direction B during operation, as described in more detail herein. Second retention plate 238 is positioned adjacent to second heater element 236 when inserted within recess 240, and is sized and oriented to maintain second heater element 236 within recess 240. In the exemplary embodiment, second retention plate 238 includes a first coupling aperture 246 and a second coupling aperture 248 that are each sized and oriented to receive fastener 224 therethrough, as described herein. In the exemplary embodiment, first and second retention plates 216 and 238 are fabricated from a polyimide, such as for example VESPEL® (E. I. Du Pont De Nemours and CO., Inc. of Wilmington, Del.). Alternatively, first and second retention plates 216 and 238 may be fabricated from any material that enables detector system 100 to function as described herein.

Desorption chamber 200 includes an outer shell 260 having a first portion 262 and a second portion 264 that when assembled defines a substantially cylindrical shape of outer shell 260. In the exemplary embodiment, first portion 262 includes a mounting flange 266 that includes a first coupling aperture 268 and a second coupling aperture 270 that are each sized and oriented to receive fastener 224 as described herein. Similarly, second portion 264 includes a mounting flange 272 that includes a first coupling aperture 274 and a second coupling aperture 276 (shown in FIG. 3) that are each sized and oriented to receive fastener 224.

In the exemplary embodiment, first heating assembly 210 and second heating assembly 232 are positioned such that heat produced by first and second heater elements 214 and 236 is emitted radially inward. First and second portions 262 and 264 of outer shell 260 are positioned about first and second heating assemblies 210 and 232 such that respective first coupling apertures 220, 228, 241, 246, 268 and 274 and second coupling apertures 222, 230, 242, 248, 270 and 276 are aligned, and a plurality of fasteners 224 are received therethrough for use maintaining first and second heating assemblies 210 and 232 therein. In the exemplary embodiment, fastener 224 is a threaded bolt configured to threadably engage with second portion coupling apertures 274 and 276. Alternatively, fastener 224 may include a rivet, a nut and bolt combination, a screw, or any fastening device that may be used to maintain first and second heating assemblies 210 and 232 in a substantially fixed positioned when placed therein and that enables detection system 100 to function as described herein. In an alternative embodiment, desorption chamber 200 includes a single heating assembly, for example heating assembly 210, having a heater element 214, a frame element 212, and a retention plate 216 assembled such that detection system 100 may function as described herein.

In the exemplary embodiment, desorption chamber 200 includes a substantially cylindrical inner sleeve 278 that is sized to receive assembled outer shell 260. Desorption chamber 200 includes a substantially cylindrical outer sleeve 280 that is sized to receive inner sleeve 278. A mounting element 282 receives a portion of outer sleeve 280 and is configured to threadably couple desorption chamber 200 to detector assembly 112 shown in FIG. 1. Alternatively, desorption chamber 200 may be coupled to detector assembly 112 using any coupling device, such as screws, bolts, or any fastener that enables detection system 100 to function as described herein.

In the exemplary embodiment, when desorption chamber 200 is assembled as shown in FIG. 3, first frame element 212 and second frame element 234 define receptacle 284 therebetween. More specifically, receptacle 284 is axially aligned with slot 126 (shown in FIG. 1) and extends inward from slot 126 such that first and second heating assemblies 210 and 232, and more particularly, first and second heater elements 214 and 236 are substantially exposed to receptacle 284 such that detection system 100 may function as described herein.

Receptacle 284 is sized and oriented to receive a sampling trap 128 (shown in FIG. 1) therein for use in particle sampling.

Figure 4:
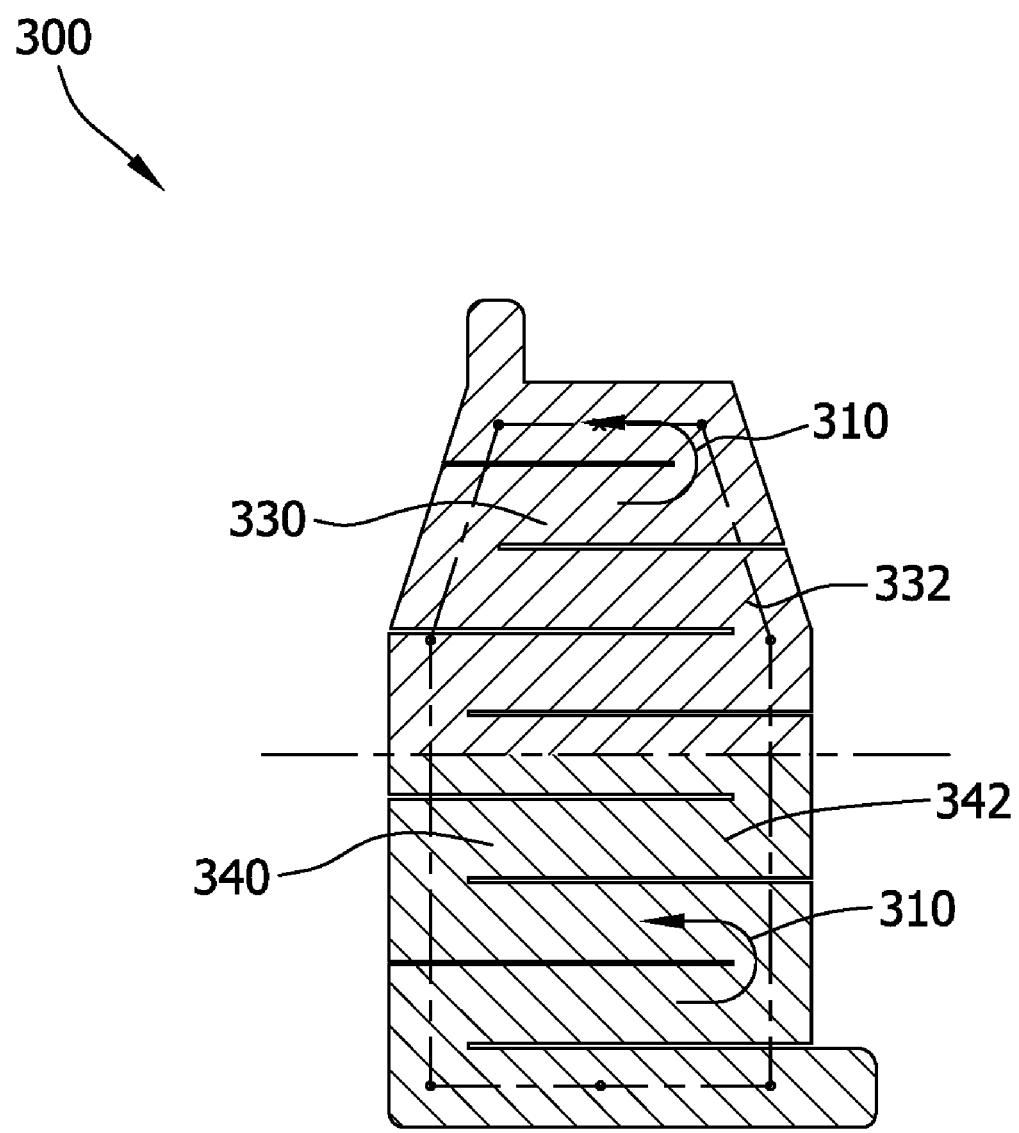
FIG. 4 is a schematic illustration of an exemplary heater element used with detection system shown in FIG. 1.

FIG. 4 is schematic illustration of an exemplary heater element 300. Heater element 300 is a substantially planar, etched metallic device that is configured to be electrically coupled to a power source (not shown) and use resistive heating to increase in temperature and transmit a heat output. In the exemplary embodiment, heater element 300 is fabricated from a nickel-cobalt ferrous alloy, such as for example KOVAR® (CRS Holdings, Inc. of Wilmington, Del.) and is etched to include a serpentine conduction path 310. Alternatively, heater element 300 may be fabricated from any alloy foil having a low thermal mass, that facilitates rapid heating thereof, and that may enable detection system 100 to function as described herein.

In the exemplary embodiment, heater element 300 is selectively coated with a polymer that enhances heater element's 300 attractive qualities when in the presence of certain analytes. More specifically, and in the exemplary embodiment, a first portion 330 of heater element is coated with a first polymer 332, such as for example Polydimethylsiloxane/Divinylbenzene (PDMS/DVB), which facilitates increasing an attractive force of heater element 300 when in the presence of certain analytes, such as for example explosives, narcotics, chemical weapons agents, and/or toxic industrial chemicals, as described in more detail herein. Moreover, a second portion 340 of heater element 300 is coated with any other such polymer, such as for example a chlorofluorocarbon (CFC) compound, which facilitates increasing an attractive force of heater element when in the presence of certain analytes. As shown in FIG. 4, first polymer 332 may be applied to first region 330 of heater element 300, and a second polymer 342 may be applied to second region 340 of heater element 300, wherein the first polymer 332 and the second polymer 342 facilitate attracting a respective first airborne sample and a different second airborne sample to heater element during operation. Alternatively, no polymer is applied to heater element 300. In an alternative embodiment, more than two polymers may be applied to heater element 300 to enable a plurality of differing airborne particulate to be attracted to a respective portion of heater element during vapor collection operations.

Figure 5:
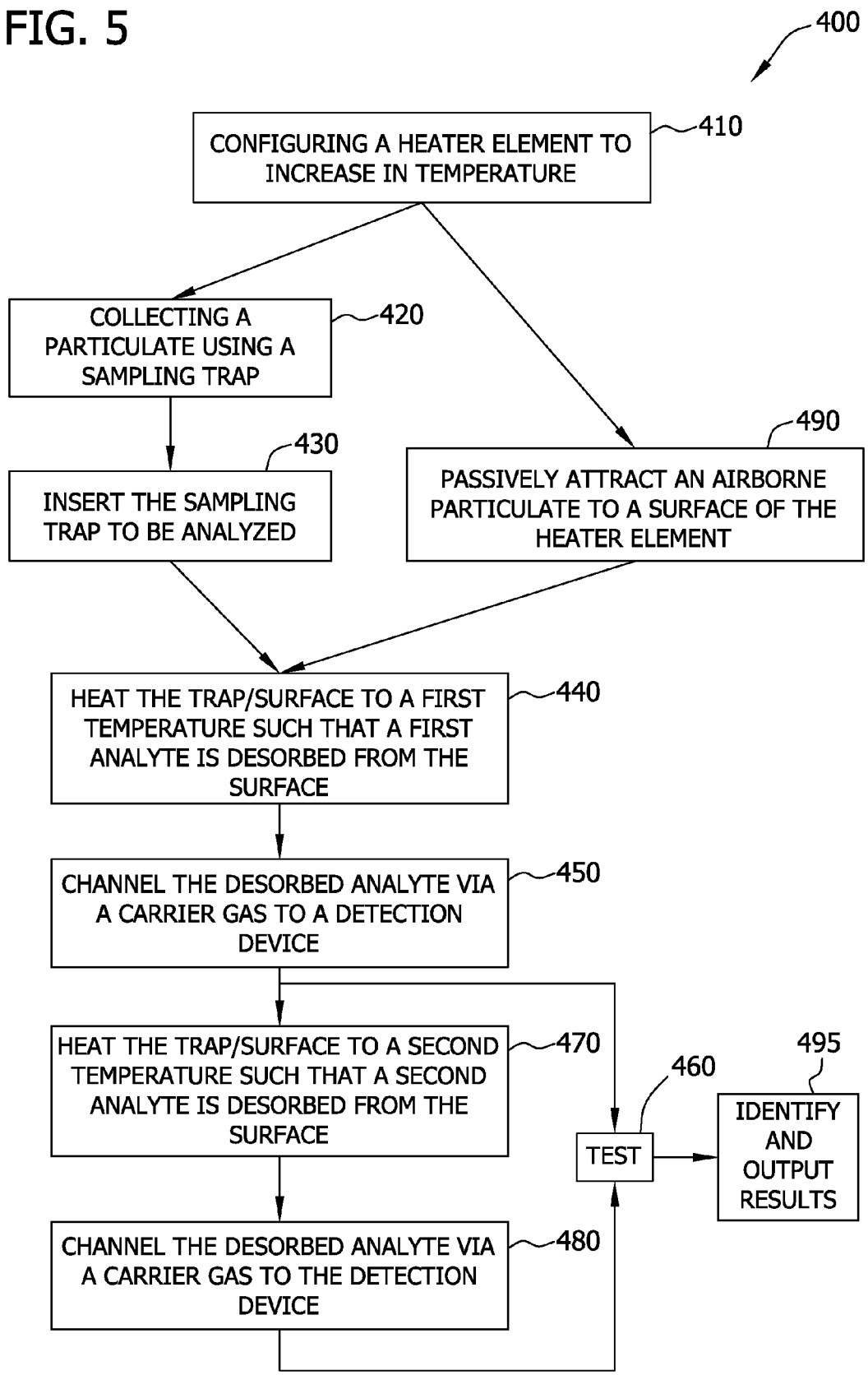
FIG. 5 is a flow diagram of an exemplary method for identifying an unknown substance using an exemplary integrated particle and vapor sampling device.

In the exemplary embodiment, detection system 100 is configured to function in both particle sampling mode and vapor sampling mode. FIG. 5 is a flow diagram of an exemplary method 400 for identifying an unknown substance using an integrated particle and vapor sampling device. In the exemplary embodiment, method 400 includes configuring 410 the heater element to increase in temperature along a predetermined temperature profile in light of the analytes to be tested. Different analytes vaporize at different temperatures. The temperature of the heater element is a function of the electrical resistance thereof, and therefore the temperature may be regulated to specified set points in light of the analytes to be detected by adjusting the electrical resistance of the heater element. A prescribed desorption profile is designed to volatilize compounds at different points during the analysis cycle. A low sampling flow rate is used to transfer the volatilized to the ion mobility spectrometer for chemical analysis. The use of such a desorption profile provides the ability to reduce false alarms.

In the exemplary embodiment, method 400 includes collecting 420 a first particulate from an external source using a sampling trap. The particulate to be tested may include for example an explosive, a narcotic, a chemical weapons agent, and/or a toxic industrial chemical. Next, the sampling trap is inserted 430 into desorption chamber of the detection system, as described herein. The sampling trap is flash heated 440 to a vaporization temperature appropriate to vaporize that particular analyte in accordance with the desorption profile described herein. Once the analyte is desorbed 440, the analyte is channeled 450 using a carrier gas into the detection device, as described herein. The desorbed analyte is then tested 460 within the detection device. In the exemplary embodiment, following testing 460, the sample is identified 495 for potential chemical threats and/or potential biological threats contained therein and that information is output to a user interface.

In the exemplary embodiment, the sampling trap is then heated 470 to a higher second temperature to desorb a second analyte present on the sampling trap, as is described herein. Once the second analyte is desorbed 470, the analyte is channeled 480 using a carrier gas into the detection device, as described herein. The second desorbed analyte is then tested 460 within the detection device to identify potential chemical threats and/or potential biological threats contained therein. In the exemplary embodiment, following testing 460, the sample is identified 495 for potential chemical threats and/or potential biological threats contained therein and that information is output to a user interface.

Alternatively, following the step of configuring 410 the heater element to increase in temperature, method 400 includes vapor sampling by passively attracting 490 the vapor to a surface of the heater element. A large volume of air is channeled through the sampling system pump. Analyte vapors in the air collect on the metal heater element surfaces by adsorption or condensation. Once the analyte is collected on the heater element surfaces, the high-volume sampling pump is stopped. The analysis cycle begins by flash heating 440 the metal foil to a prescribed temperature/time profile, as described herein. Once the first analyte or a group of analyte is desorbed 440, the analyte(s) are channeled 450 using a carrier gas into the detection device. The desorbed analytes are then tested 460 within the detection device to identify potential chemical threats and/or potential biological threats contained therein. In the exemplary embodiment, following testing 460, the sample is identified for potential chemical threats and/or potential biological threats contained therein and that information is output to a user interface.

In the exemplary embodiment, heater element is then heated 470 to a higher second temperature to desorb a second analyte or a group of analyte present on heater element. Once the second group of analytes are desorbed 470 from the surface of the heater, the analyte channeled 480 using a carrier gas into the detection device, as described herein. The second desorbed analytes are then tested 460 within the detection device to identify potential chemical threats and/or potential biological threats contained therein.

During use, such a system may be operated in either the particulate or vapor monitoring mode without physically changing the sampling system. This has significant time savings to the operator and allows for the detection of a wider variety of compounds present in vapor or particulate mode.

Figure 6:
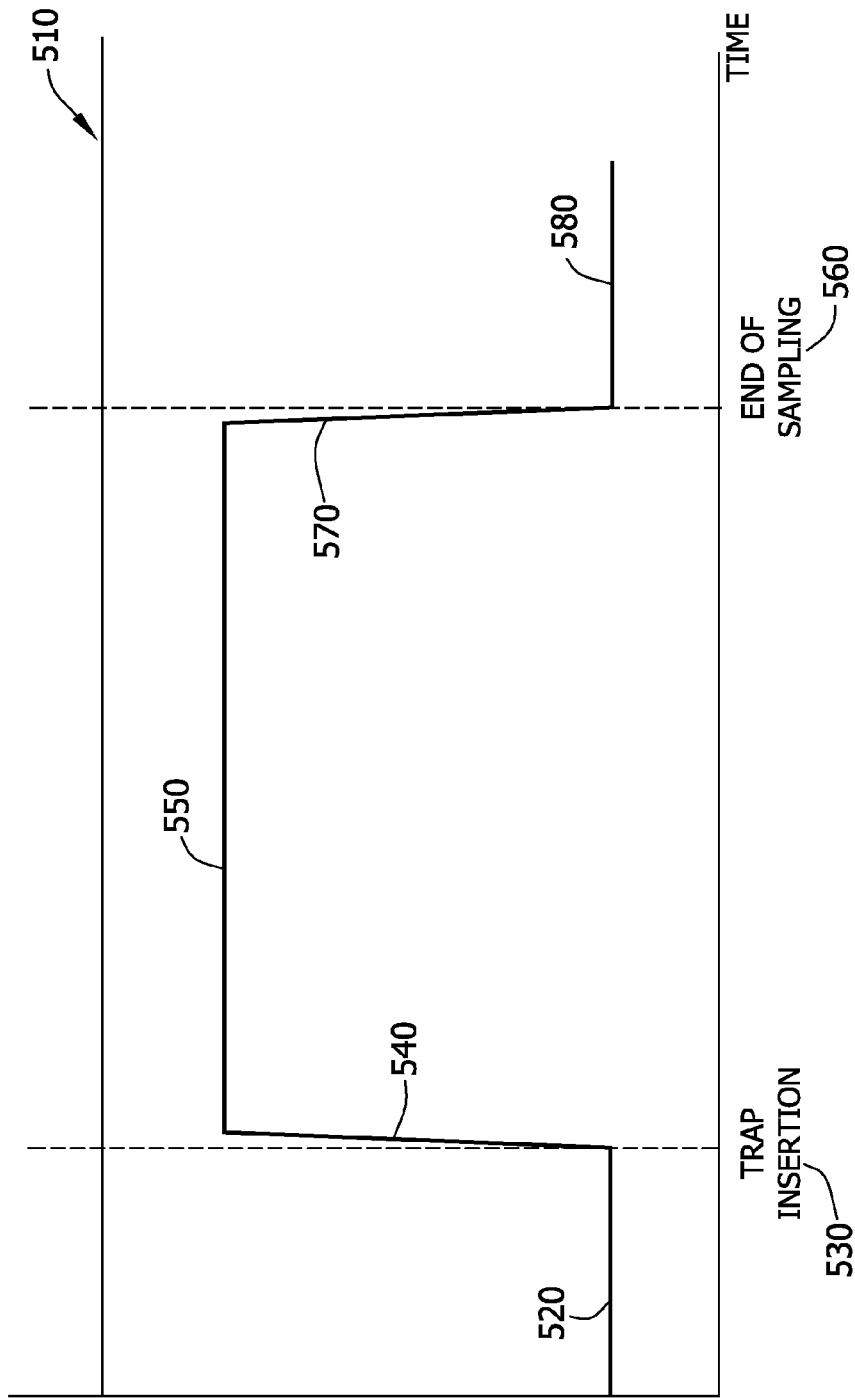
FIG. 6 is a graphical illustration of an exemplary heating profile for detection system in a particle detection mode.

FIG. 6 is a graphical illustration of an exemplary heating profile 500 for an exemplary detection system in a particle detection mode. In particle sampling mode, detection system is maintained at and adjusted to a constant temperature 510 prior to activation, and sampling pump is maintained in an off configuration 520. A sampling trap is inserted 530 into detection system as described herein, and sampling pump increases the air flow rate 540 through the detection system to a predetermined level 550. In the exemplary embodiment, air flow rate therethrough is approximately 200 cubic centimeters per minute (cc/min). Alternatively, sampling pump may provide any air flow rate that enables detection system 100 to function as described herein. At an end of the sampling time 560, the sampling pump returns 570 to an off configuration 580. In the exemplary embodiment, detection system 100 includes a sensor 590 (shown in FIG. 2) that detects insertion of sampling trap 128 (shown in FIG. 1) into detection system 100 and substantially automatically activates sampling pump 116 in response thereto while in particle detection mode.

Figure 7:
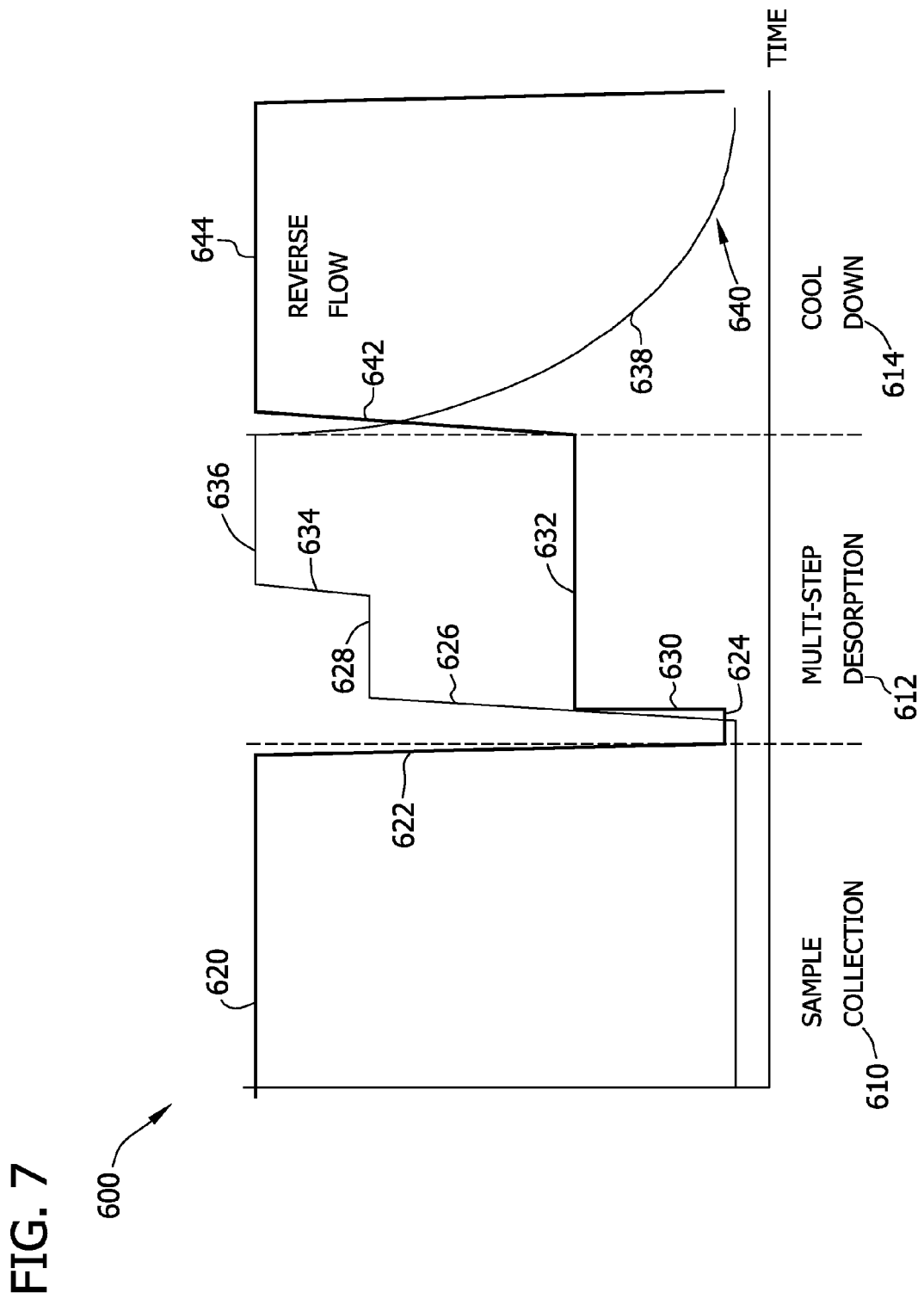
FIG. 7 is a graphical illustration of an exemplary heating profile for detection system in a vapor sampling mode.

FIG. 7 is a graphical illustration of an exemplary heating profile 600 for an exemplary detection system 100 in a vapor sampling mode. In the exemplary embodiment, vapor sampling mode includes a sample collection period 610, a desorption period 612 and a cool down period 614. During sample collection period 610, a large volume of air is channeled through the desorption chamber via the sampling pump. In the exemplary embodiment, an air flow rate 620 therethrough is approximately 2000 cc/min. Alternatively, sampling pump may provide any air flow rate 620 during sample collection that enables detection system to function as described herein.

At the start of desorption period 612, sampling pump is decreased 622 to 0 cc/min 624 and heater element is flash heated 626 to a first desorption temperature 628. In the exemplary embodiment, flash heating 626 of the heater element occurs within a time of less than approximately one second. The temperature of the heater element is accurately and rapidly determined since heater element temperature is a function of the resistance used to increase the heat of the heater element. In an alternative embodiment, temperature of the heater element may be controlled by using an infrared sensor coupled to the heater element. At first desorption temperature 628, sampling pump is activated 630 to enable an air flow rate 632 sufficient for data collection, and the desorbed analyte from the heater element is channel to the desorption chamber via this air flow for testing. Note that the sample pump can be activated immediately after the sampling is completed or a delay of the sampling pump may be programmed in the system.

In the exemplary embodiment, the temperature of heater element is further increased 634 to a second temperature 636 to facilitate desorbing a second analyte or a group of analytes present on the heater element. The desorbed analyte is channeled to the desorption chamber via this air flow for testing.

In the exemplary embodiment, the heater is cooled down immediately after the desorption phase is completed. During cool down 614, electrical current being provided to the heater element is ceased and heater element is allowed to cool 638 to ambient temperatures 640, while sampling pump is activated 642 in a reverse flow configuration 644 to discharge a flow of air across heater element to facilitate cooling heater elements to ambient temperature. During operation, such a system is configured to sample both particles and vapors without physically changing the sampling system on the ion mobility spectrometer. The disclosed system also utilizes controlled, multi-step desorption heating profile to improve selectivity across a wide range of analytes with a time resolution of less than 0.1 seconds.

Exemplary embodiments of detection systems that incorporate vapor sampling and particle sampling into an integrated device are described in detail above. The above-described systems are configured to assess the chemical composition and/or biological nature or identity of an unknown substance or material to facilitate identifying potential chemical threats and/or potential biological threats. The systems and methods described herein represent sample collection devices that may sample both particles and vapors without the need to physically change the sampling system on the ion mobility spectrometer. Such a system may be adjusted from a vapor sampling mode to particulate sampling mode (or vice versa) rapidly without the need for recalibration. This has significant time savings to the operator and allows for the detection of a wider variety of compounds, as particle sampling is better suited for lower vapor-pressure compounds and vapor mode sampling is better suited for higher vapor-pressure compounds. The ability to sample both vapors and particles without a significant equipment changeover is a significant advantage over existing technologies.

The systems and method described herein also allow a user to utilize a desorption heating profile to improve selectivity across a wide range of analytes. The system is designed with a low thermal mass and therefore may rapidly increase in temperature. Since different compounds vaporize at different temperatures the system can selectively vaporize (desorb) compounds at different times as the temperature of the sampling system increases. This difference in desorption can be used to differentiate interferents from compounds of interest.

Although the foregoing description contains many specifics, these should not be construed as limiting the scope of the present disclosure, but merely as providing illustrations of some of the presently preferred embodiments. Similarly, other embodiments may be devised which do not depart from the spirit or scope of the present disclosure. Features from different embodiments may be employed in combination. The scope of the disclosure is, therefore, indicated and limited only by the appended claims and their legal equivalents, rather than by the foregoing description. All additions, deletions and modifications as disclosed herein which fall within the meaning and scope of the claims are to be embraced thereby.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

This written description uses examples to support the claims, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A detection system for identifying an unknown substance, said detection system comprising:
a desorption chamber configured to receive a sampling trap;
a detector assembly configured to receive a sample vapor and determine a substance contained within the vapor;
at least one heater element operatively coupled in flow communication with said detector assembly, said at least one heater element configured to;
attract an airborne sample when said detection system is in a vapor mode; and
desorb at least a portion of the attracted sample when said detection system is in a vapor mode;

wherein said at least one heater element comprises a coating applied to at least a portion of a surface of said at least one heater element, said coating facilitates attracting the airborne sample; and wherein said at least one heater element is positioned proximate to said desorption chamber and configured to increase a surface temperature of said sampling trap to facilitate desorbing the attracted sample from said sampling trap when said sampling trap is positioned within said desorption chamber.

2. A detection system in accordance with claim 1, wherein said coating comprises a first polymer applied to a first region of said at least one heater element, and a second polymer applied to a second region of said at least one heater element, wherein said first polymer facilitates attracting a first airborne sample and said second polymer facilitates attracting a second airborne sample.

3. A detection system for identifying an unknown substance, said detection system comprising:
a detector assembly configured to receive a sample vapor and determine a substance contained within the vapor;
at least one heater element operatively coupled in flow communication with said detector assembly, said at least one heater element configured to;
attract an airborne sample when said detection system is in a vapor mode; and
desorb at least a portion of the attracted sample when said detection system is in a vapor mode;
wherein said at least one heater element comprises a coating applied to at least a portion of a surface of said at least one heater element, said coating facilitates attracting the airborne sample; and
wherein said at least one heater element is configured to attract the airborne sample at a first temperature, and desorb the airborne sample at a second temperature, wherein the second temperature is greater than the first temperature.

4. A detection system in accordance with claim 1, wherein said at least one heater element has a serpentine conduction path, said at least one heater element configured to increase in temperature using resistive heating.

5. A detection system in accordance with claim 4, wherein said at least one heater element is configured to increase to a first temperature to desorb a first portion of a sample, wherein said at least one heater element is further configured to increase to a second temperature to desorb a second portion of a sample.

6. An apparatus for integrated particle and vapor sampling, said apparatus comprising a plurality of heater elements positioned about a desorption chamber, said apparatus configured to attract a quantity of an airborne sample, and desorb a quantity of the airborne sample to form a concentrated vapor, wherein each heater element of said plurality of heater elements comprises a coating applied to at least a portion of a surface of each heater element, wherein said coating facilitates attracting the airborne sample and wherein said desorption chamber further comprises at least one slot configured to receive a sampling trap, wherein said plurality of heater elements are configured to increase a surface temperature of said sampling trap such that at least a portion of particulate sample is desorbed from said sampling trap when positioned within said desorption chamber.

7. An apparatus in accordance with claim 6, wherein said coating comprises a first polymer positioned within a first region of said at least one heater element, and a second polymer positioned within a second region of said at least one heater element, wherein said first polymer facilitates attracting a first airborne sample to said first region and said second polymer facilitates attracting a second airborne sample to said second region.

8. An apparatus in accordance with claim 6, wherein at least one heater element of said plurality of heater elements has a serpentine conduction path, said at least one heater element configured to increase in temperature using resistive heating.

9. An apparatus in accordance with claim 8, wherein said plurality of heater elements are configured to increase to a first temperature to desorb a first airborne sample, wherein said at least one heater element is further configured to increase to a second temperature to desorb a second airborne sample.

10. An apparatus in accordance with claim 6, wherein said plurality of heater elements is configured to attract the airborne sample of at least one of an explosive, a narcotic, a chemical weapons agent, and a toxic industrial chemical.

11. A method for identifying an unknown substance using an integrated particle and vapor sampling device, said method comprising:
collecting a sample on a surface of at least one of a heater element and a sampling trap, wherein a coating is applied to at least a portion of a surface of the at least one heater element, wherein the coating facilitates attracting a first particulate or a vapor of the sample;
heating the surface to a first temperature to desorb a first portion of the sample from the surface; and
channeling the first portion of the sample via a carrier gas to a detection device to facilitate determining a substance contained within the first portion of the sample.

12. A method in accordance with claim 11, wherein collecting the sample further comprises at least one of:
using a sampling trap to collect the sample in particulate form;
passively attracting the sample to a surface of the heater element; and
configuring the heater element to increase in temperature to facilitate desorbing the sample from either the heater surface or the sampling trap.

13. A method in accordance with claim 11, wherein said applying a coating comprises applying a first polymer to a first region of the heater element, and applying a second polymer to a second region of the heater element, wherein the first polymer facilitates attracting a first group of analyte to the first region and the second polymer facilitates attracting a second group of analyte to the second region.

14. A method in accordance with claim 13, further comprising heating the surface to a second temperature such that the second group of analyte is desorbed from the surface.

15. A method in accordance with claim 14, wherein heating the surface to a second temperature further comprises using resistive heating to increase the temperature of the surface.

16. A detection system in accordance with claim 5, wherein said at least one heater element is further configured to increase in temperature to desorb at least a third portion of the sample.

17. An apparatus in accordance with claim 9, wherein said at least one heater element is further configured to increase in temperature to desorb at least a third airborne sample.

* * * * *